United States Patent
Claoue

(10) Patent No.: US 7,410,500 B2
(45) Date of Patent: Aug. 12, 2008

(54) INTRAOCULAR LENS

(75) Inventor: Charles Claoue, London (GB)

(73) Assignee: Rayner Intraocular Lenses Ltd, Buckinghamshire (GB)

( * ) Notice: Subject to any disclaimer, the term of this patent is extended or adjusted under 35 U.S.C. 154(b) by 0 days.

(21) Appl. No.: 10/496,206

(22) PCT Filed: Nov. 28, 2002

(86) PCT No.: PCT/GB02/05360

§ 371 (c)(1),
(2), (4) Date: Oct. 25, 2004

(87) PCT Pub. No.: WO03/047466

PCT Pub. Date: Jun. 12, 2003

(65) Prior Publication Data

US 2005/0049699 A1    Mar. 3, 2005

(30) Foreign Application Priority Data

Nov. 30, 2001 (GB) ................................. 0128762.2

(51) Int. Cl.
*A61F 2/16* (2006.01)
(52) U.S. Cl. ..................... 623/6.26; 623/6.25
(58) Field of Classification Search ................. 623/6.26
See application file for complete search history.

(56) References Cited

U.S. PATENT DOCUMENTS

| | | | | |
|---|---|---|---|---|
| 3,628,854 A | * | 12/1971 | Jampolsky | .................. 351/175 |
| 4,581,031 A | * | 4/1986 | Koziol et al. | ............... 623/6.26 |
| 4,601,545 A | * | 7/1986 | Kern | .......................... 349/200 |
| 4,828,558 A | | 5/1989 | Kelman | |
| 5,135,592 A | | 8/1992 | Melvin | |
| 5,152,788 A | | 10/1992 | Isaacson et al. | |
| 5,674,282 A | | 10/1997 | Cumming | |
| 6,197,057 B1 | | 3/2001 | Peyman et al. | |

FOREIGN PATENT DOCUMENTS

| | | | |
|---|---|---|---|
| EP | 276331 A1 | * | 8/1988 |
| EP | 0 458 508 A2 | | 11/1991 |
| JP | 02019146 A | * | 1/1990 |

OTHER PUBLICATIONS

Reflexite brochure: Display Optics.*

* cited by examiner

*Primary Examiner*—Dave Willse
*Assistant Examiner*—Javier G Blanco
(74) *Attorney, Agent, or Firm*—Saliwanchik, Lloyd & Saliwanchik

(57) ABSTRACT

An intraocular lens comprises, as one face thereof, a Fresnel prism. Such a lens can be used for the treatment of a macular condition requiring a change of focus, e.g. age-related macular degeneration.

3 Claims, 1 Drawing Sheet

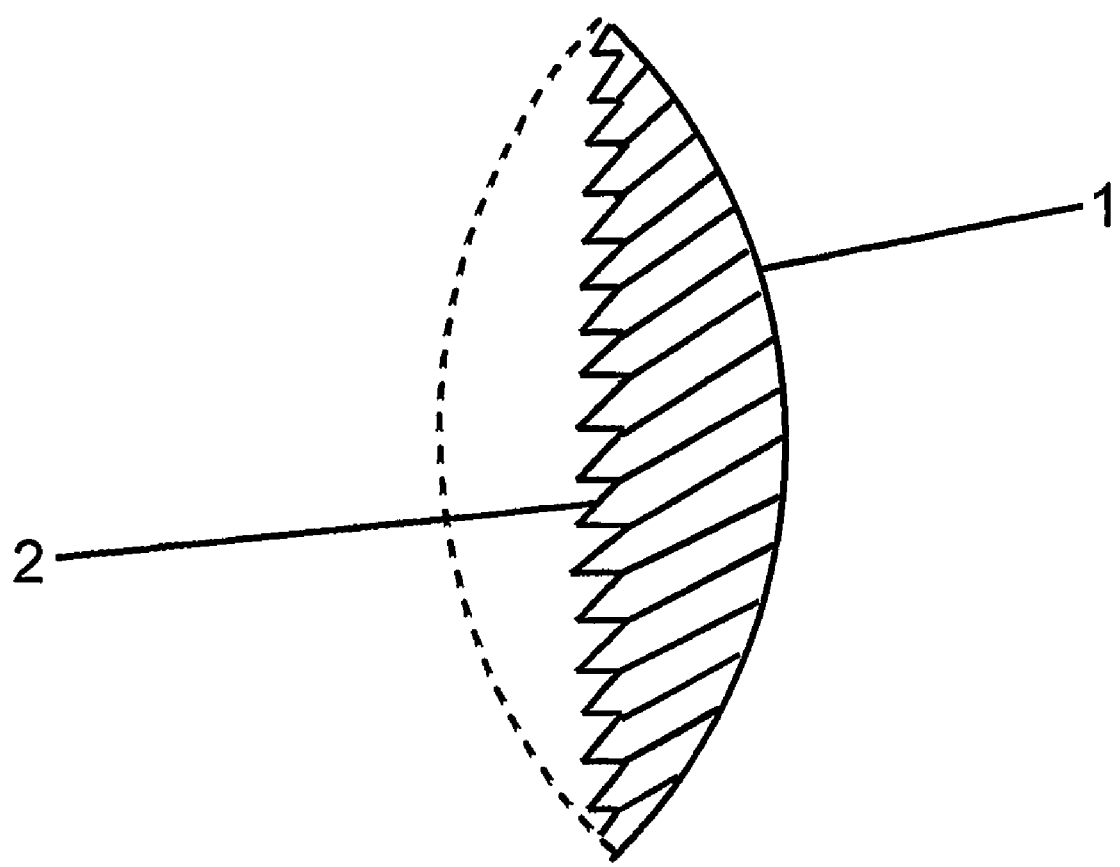

INTRAOCULAR LENS

This application is a National Stage Application of International Application Number PCT/GB02/05360, filed Nov. 28, 2002; which claims priority to Great Britain Application GB 0128762.2, filed Nov. 30, 2001.

FIELD OF THE INVENTION

This invention relates to an intraocular lens (IOL), and in particular to an intraocular lens that can be used to reduce the effects of age-related macular degeneration (ARMD).

BACKGROUND OF THE INVENTION

The treatment of focal macular diseases, and in particular ARMD, represents a major problem. Since the intact macula provides the vision that is required for reading, driving etc (but not for peripheral vision), the fact that there is no effective treatment for its degeneration means that many people increasingly retain peripheral vision only.

In order to solve this problem, it has been proposed that the retina should be moved. A more practical solution is to move the image from the macula to a point on the retina where there are healthy cells; although these cells may not function as well as the macular cells, an adequate degree of vision may be retained. Among other things, this is proposed in U.S. Pat. No. 6,197,057.

In particular, each of FIGS. 25, 27, 31 and 33 of U.S. Pat. No. 6,197,057 discloses a supplemental lens, i.e. an intraocular lens that is provided in addition to the natural, crystalline lens or to a biconvex IOL. All these drawings show a supplemental lens that is a conventional prism. The consequence is that the image is moved, away from the macula. Elsewhere in the specification, it is suggested that a Fresnel lens should be used as the supplemental IOL (column 9 line 13), and also that the lens should be "fresnel-shaped" (claim 14; again, this is in the context of a supplemental lens). It is unclear what form the "fresnel-shaped" lens should take.

SUMMARY OF THE INVENTION

The present invention is based at least in part on the realisation that, while the treatment of ARDM requires removal of the crystalline lens, the focusing power of the IOL that is used instead can be provided by a conventional lens, while that same lens can be modified so that light is focused on a (healthy) part of the retina that is not the macula. The present invention takes account of the fact that it would be undesirable to use a prism for this purpose, since that would be unnecessarily bulky, and accepts that a Fresnel prism would not normally be used because of image degradation; the latter is a factor of relatively little importance if the macula is anyway degraded. According to the present invention, an intraocular lens comprises, as one face thereof, a Fresnel prism.

The novel lens provides the necessary features within a single unit. It is therefore easier to use and less bulky than any known IOL having the same function. It can be thin and light. Although it will degrade the image, this is a minor disadvantage and, in any case, the retina may not have good resolution.

DESCRIPTION OF THE INVENTION

The invention will now be illustrated by way of example only with reference to the accompanying drawing which is a schematic cross-sectional view of a lens embodying the present invention. The lens comprises what is essentially one half of a conventional lens, having a curved surface 1, and an opposed surface 2 in the form of a Fresnel prism.

A lens of the invention may be of conventional size and may be made of any suitable material. General characteristics of such lenses are known. The novel lens may be made of a rigid or hydrophilic material. Suitable materials are those used for intraocular lenses and include both hydrophobic and hydrophilic polymers containing acrylate and methacrylate such as polymethyl methacrylate, and silicone elastomers such as dimethylsiloxane.

If necessary or desired, a lens of the invention may include one, two or more haptics. As is known, they may be attached to the body of the lens at its perimeter, and may extend radially or tangentially.

A lens of the invention will usually have only one power. A range of lenses may be produced, each having a different power. Alternatively, "piggy-backing" may be used, by the provision of a supplemental lens that changes the power of a lens according to the invention.

The novel lens may be used in the eye, in either orientation, but it is generally preferred that a smooth face should face the posterior capsule. That face of the lens having the Fresnel prism may be made smooth, by covering it with a translucent material (to the extent shown by the dotted line in the drawing).

The Fresnel prism component itself may have any of a variety of suitable designs. These include planar (flat disc), cylindrical (curved disc) and spherical (meniscus disc).

A lens of the invention may be used, following removal of the crystalline lens, for the treatment of any macular condition requiring a change of focus. The novel lens is particularly useful for treatment of ARMD. Its function may be visualised by substituting such a lens for the crystalline lens/IOL plus supplementary lens shown in FIGS. 25, 27, 31 and 33 of U.S. Pat. No. 6,197,057.

The invention claimed is:

1. A method for the treatment of a macular condition requiring a change of focus, which comprises replacing a patient's crystalline lens with an intraocular lens comprising, as one face thereof, a Fresnel prism, wherein the Fresnel prism is positioned as part of the intraocular lens such that incident light striking the intraocular lens is deviated and an image is moved away from the macula.

2. The method according to claim 1, wherein the macular condition is age-related macular degeneration.

3. The method according to claim 1, wherein said method comprises replacing a patient's crystalline lens with a composite intraocular lens comprising an intraocular lens comprising, as one face thereof, a Fresnel prism and also a material covering said one face, so that the composite intraocular lens has a smooth surface.

* * * * *